United States Patent
Tanabe et al.

(10) Patent No.: US 8,760,544 B2
(45) Date of Patent: Jun. 24, 2014

(54) LIGHT OR RADIATION IMAGE PICKUP APPARATUS

(75) Inventors: Koichi Tanabe, Uji (JP); Hiroyuki Kishihara, Kizugawa (JP)

(73) Assignee: Shimadzu Corporation, Kyoto (JP)

( * ) Notice: Subject to any disclaimer, the term of this patent is extended or adjusted under 35 U.S.C. 154(b) by 261 days.

(21) Appl. No.: 13/265,064

(22) PCT Filed: Apr. 24, 2009

(86) PCT No.: PCT/JP2009/001895
§ 371 (c)(1),
(2), (4) Date: Oct. 18, 2011

(87) PCT Pub. No.: WO2010/122609
PCT Pub. Date: Oct. 28, 2010

(65) Prior Publication Data
US 2012/0033110 A1 Feb. 9, 2012

(51) Int. Cl.
*G01T 1/24* (2006.01)
*H04N 9/64* (2006.01)

(52) U.S. Cl.
USPC .................. 348/244; 250/370.11; 250/370.15

(58) Field of Classification Search
CPC ....... H04N 5/32; H04N 5/3205; H04N 5/325; G01T 1/20–1/208; H01L 27/14658–27/14663; H01L 27/14676
USPC ............ 348/244; 250/370.09, 370.11, 370.15
See application file for complete search history.

(56) References Cited

U.S. PATENT DOCUMENTS

| | | | |
|---|---|---|---|
| 6,344,370 B1* | 2/2002 | Izumi et al. | 438/97 |
| 6,927,795 B1* | 8/2005 | Cazier et al. | 348/243 |
| 7,049,598 B1* | 5/2006 | Jordanov et al. | 250/363.01 |
| 2004/0051796 A1* | 3/2004 | Kelly et al. | 348/243 |
| 2005/0242380 A1 | 11/2005 | Suzuki et al. | |
| 2007/0263111 A1* | 11/2007 | Satodate | 348/311 |
| 2007/0273775 A1* | 11/2007 | Jiang | 348/244 |

FOREIGN PATENT DOCUMENTS

| | | | |
|---|---|---|---|
| JP | 2005-312805 A | 11/2005 | |
| JP | 2006-305228 A | 11/2006 | |

OTHER PUBLICATIONS

International Search Report for the Application No. PCT/JP2009/001895 mailed Jul. 7, 2009.

\* cited by examiner

*Primary Examiner* — Sinh Tran
*Assistant Examiner* — Mark Monk
(74) *Attorney, Agent, or Firm* — Cheng Law Group, PLLC

(57) ABSTRACT

The radiation image pickup apparatus of this invention can obtain an accurate temperature characteristic of dark current noise, the dark current noise being caused by dark current flowing through an X-ray conversion layer, by obtaining dark image signals at varied times for accumulating in capacitors charge signals converted by an X-ray converting layer. Consequently, the noise due to the dark current can be removed with high accuracy by removing periodically acquired offset signals from X-ray detection signals acquired at a time of X-ray image pickup, and correcting variations of the dark current noise due to a difference in temperature between a time of offset signal acquisition and the time of X-ray image pickup, using the temperature characteristic of the dark current noise.

7 Claims, 8 Drawing Sheets

LIGHT OR RADIATION IMAGE PICKUP APPARATUS

TECHNICAL FIELD

This invention relates to a light or radiation image pickup apparatus for use in the medical field or industrial field such as in non-destructive testing, RI (Radio Isotope) inspection and optical inspection, and more particularly to a light or radiation image pickup apparatus for correcting noise caused by temperature variations of a conversion layer which converts light or radiation into electric charge signals.

BACKGROUND ART

Conventionally, a light or radiation image pickup apparatus has a light or radiation detector for detecting light or radiation. Light herein refers to infrared rays, visible light, ultraviolet rays, radiation, gamma rays and so on. X-rays in particular will be described by way of example. As an X-ray detector, a flat panel X-ray detector is in wide use which detects X-rays using an active matrix substrate. This is because the active matrix substrate is very useful in that X-ray detection values can be read on a pixel-by-pixel basis. Further, where an X-ray conversion layer consisting of a semiconductor is laminated on the active matrix substrate, an X-ray detecting element can be formed for each active element.

When a semiconductor layer is used as the X-ray conversion layer, X-rays incident on the X-ray conversion layer can be converted into charge signals (carriers). These converted charge signals are stored in capacitors provided for the respective X-ray detecting elements. The stored charge signals are read by the active matrix substrate for the respective X-ray detecting elements, and are further amplified while being converted from the charge signals into voltage signals. Based on these voltage signals, an image processor can construct an X-ray transmission image.

The voltage signals sent to the image processor in this way include, besides the voltage signals based on the charge signals converted from X-rays, noise signals which are voltage signals caused by dark current in the X-ray conversion layer, and voltage signals caused by amplifier noise generated when amplifying while converting from the charge signals into the voltage signals.

With amorphous selenium (α-Se) film conventionally employed as the X-ray conversion layer, the noise signals caused by dark current do not greatly change in response to temperature change. Since the amplifier noise does not change greatly in response to temperature change, either, dark image signals (hereinafter called offset signals) occurring when X-rays are not emitted are periodically measured, and these offset signals are removed as noise signals as in Patent Document 1, for example.

PATENT DOCUMENT 1

Unexamined Patent Publication No. 2006-305228

DISCLOSURE OF THE INVENTION

Problem to be Solved by the Invention

However, in the case of the X-ray conversion layer being, for example, a CdTe polycrystalline compound semiconductor film in which noise signals caused by dark current change remarkably in response to temperature change, a problem has arisen that the periodic measurement of offset signals as in the prior art cannot correct the noise signals between the periods.

This invention has been made having regard to the state of the art noted above, and its object is to provide a light or radiation image pickup apparatus which can remove dark current noise signals in response to temperature change of a conversion layer sensitive to light or radiation.

Means for Solving the Problem

To fulfill this object, this invention provides the following construction.

A light or radiation image pickup apparatus of this invention comprises a conversion layer for converting light or radiation into charge signals; capacitors for accumulating the charge signals for detecting elements, respectively, dividing the conversion layer into a two-dimensional matrix form; a reading device for reading the charge signals accumulated in the capacitors; a charge-to-voltage converting device for converting the charge signals read from the reading device into voltage signals; a temperature measuring device for measuring temperatures of the conversion layer; and a dark current noise calculating unit for calculating dark current noises generating from dark current flowing through the conversion layer, from a dark current noise temperature characteristic obtained beforehand at times of dark images by varying time for accumulating the charge signals in the capacitors, and the temperatures measured by the temperature measuring device.

According to the light or radiation image pickup apparatus of this invention, light or radiation is converted into charge signals in the conversion layer, the converted charge signals are accumulated in the capacitors for the respective detecting elements, and the accumulated charge signals are read by the reading device and converted into voltage signals by the charge-to-voltage converting device. At this time, the dark current flowing through the conversion layer is also converted into voltage signals, to generate dark current noise. The dark current noise can be calculated with high accuracy by obtaining a temperature characteristic of this dark current noise beforehand. The temperature characteristic of noise signals caused by the dark current can be obtained with high accuracy since the temperature characteristic is obtained by changing time for accumulating the charge signals in the capacitor at a time of dark images. The dark current noise calculating unit applies a temperature sent from the temperature measuring device to this temperature characteristic, thereby to calculate a signal value of the dark current noise at that temperature with high accuracy.

The apparatus may comprise a dark image signal removing unit for removing dark image signals from the voltage signals read from the conversion layer; a noise variation calculating unit for calculating a variation between a dark current noise at a temperature at a time of dark image signal acquisition and a dark current noise at a temperature at a time of image pickup; and a noise variation removing unit for removing the dark current noise variation calculated by the noise variation calculating unit from the voltage signals read from the conversion layer. Consequently, what is necessary is just to calculate and remove only the variation for the dark current noise at the time of acquiring dark image signals, it is not necessary to acquire the dark image signals frequently, and the temperature correction of dark current noise can be made with high accuracy even when emitting light or radiation continuously.

By acquiring the dark image signals periodically, a highly accurate temperature correction can be made of noise components gently varying with temperature variations. Instead of acquiring the dark image signals periodically, a reference may be set beforehand for the temperatures measured by the temperature measuring device at the time of acquiring the dark images, and a temperature determiner may be provided for comparing this reference value and the temperatures measured at intervals of time by the temperature measuring device. When the temperatures measured at intervals of time by the temperature measuring device exceed the reference set beforehand for the temperatures measured by the temperature measuring device at the time of acquiring the dark images, the temperature determiner carries out control to acquire dark image signals, whereby a highly accurate temperature correction can be made of noise components gently varying with temperature variations.

The dark current noise temperature characteristic may be an approximate expression, or may be a look-up table. The approximate expression enables a highly accurate temperature correction of noise. The look-up table can speed up the temperature correction.

The conversion layer may be a polycrystalline compound semiconductor. The polycrystalline compound semiconductor can form a conversion layer with easy crystal growth and a large area. As a specific example, CdTe or CdZnTe is used as a main raw material. This realizes a conversion layer having excellent response to light or radiation and excellent conversion efficiency Effects of the Invention According to the light or radiation image pickup apparatus of this invention, the light or radiation image pickup apparatus provided can remove dark current noise signals in response to temperature change of a conversion layer sensitive to light or radiation.

DESCRIPTION OF REFERENCE

Figure 1:
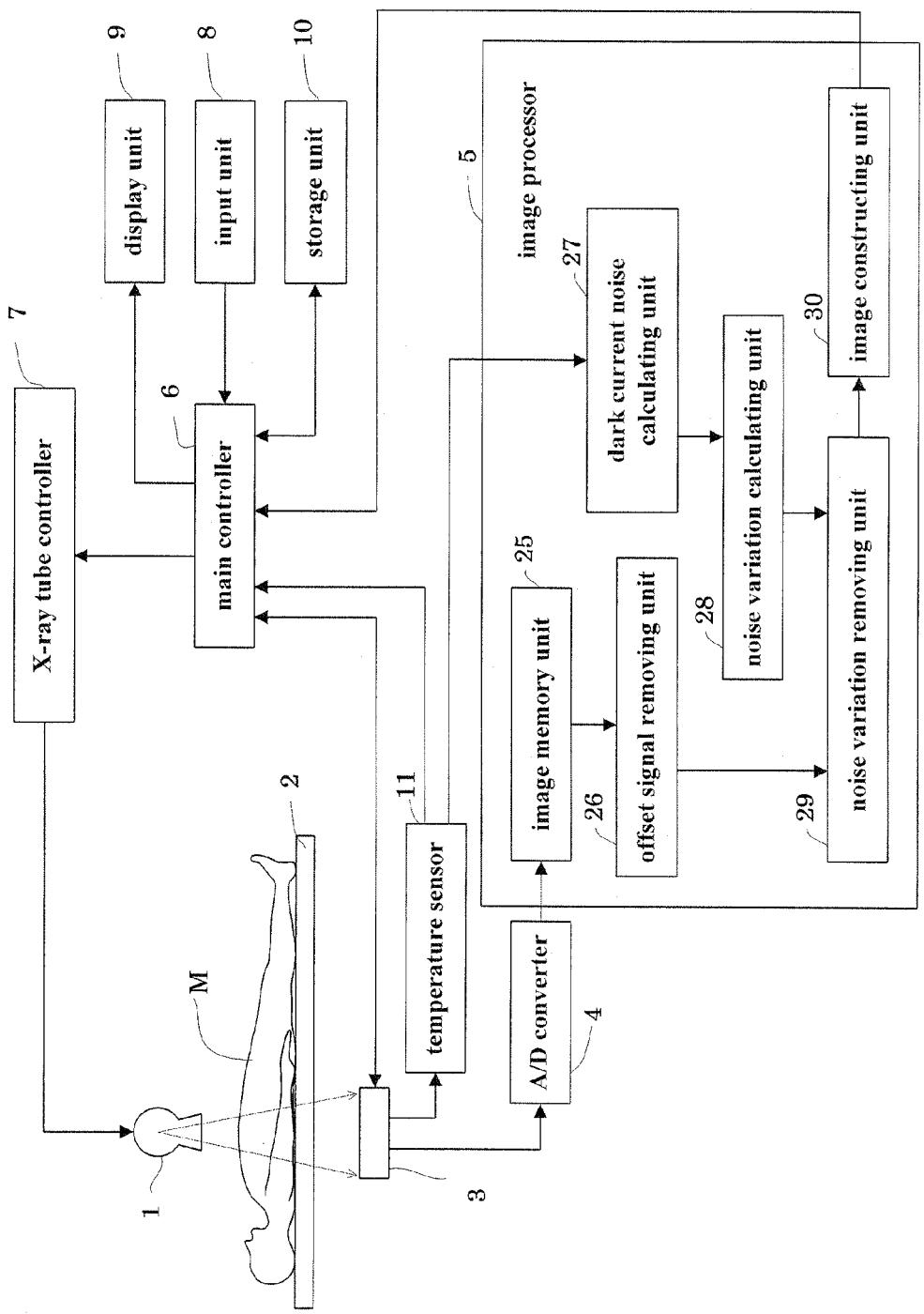
FIG. 1 is a block diagram showing an overall construction of an X-ray image pickup apparatus according to an embodiment.

3 . . . flat panel X-ray detector (FPD)
5 . . . image processor
11 . . . temperature sensor
13 . . . gate drive circuit
14 . . . charge-to-voltage converter
19 . . . X-ray conversion layer
20 . . . active matrix substrate
26 . . . offset signal removing unit
27 . . . dark current noise calculating unit
28 . . . noise variation calculating unit
29 . . . noise variation removing unit
31 . . . temperature determiner
DU . . . X-ray detecting elements
Ca . . . capacitors Embodiment An embodiment of this invention will be described hereinafter with reference to the drawings.

Figure 2:
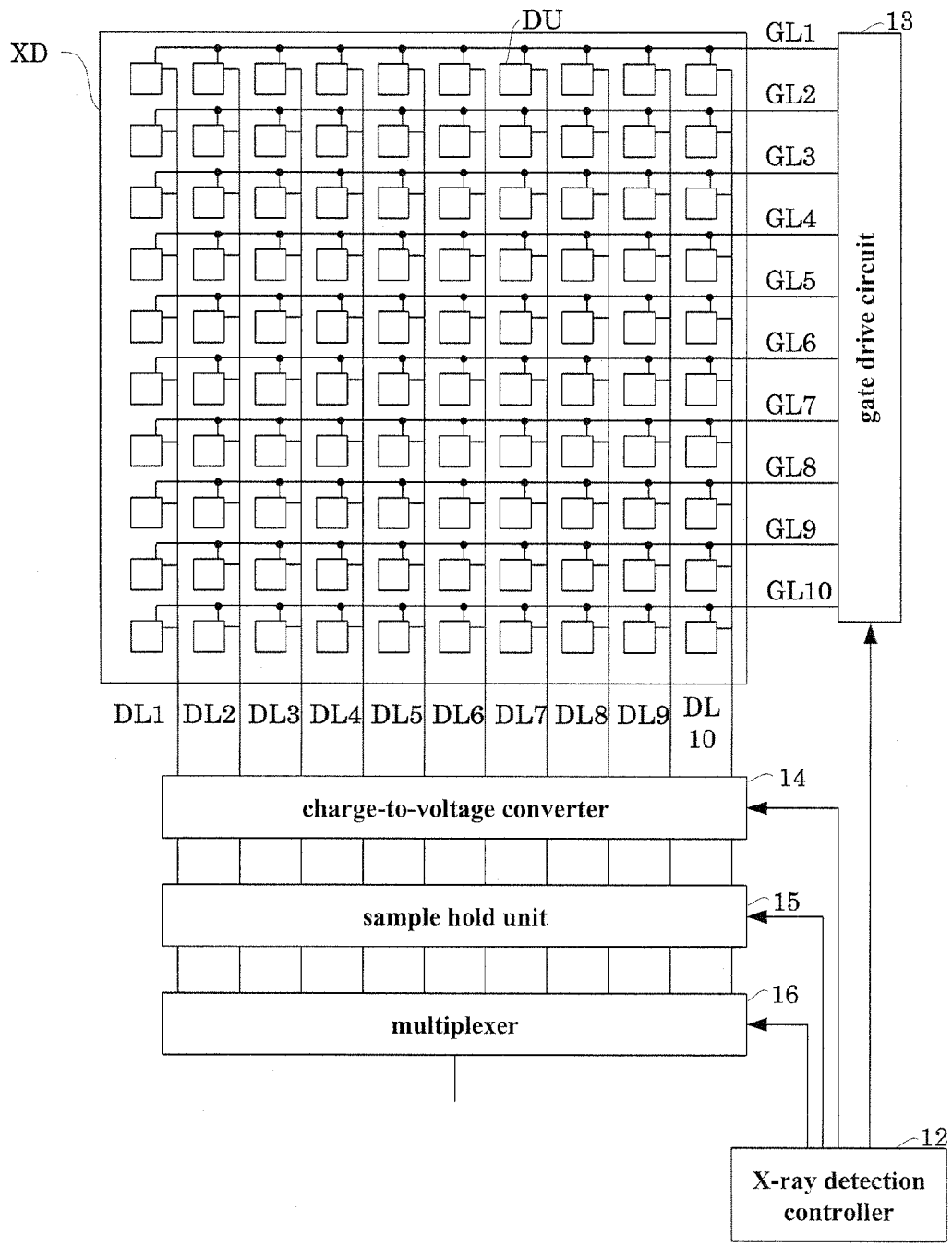
FIG. 2 is a block diagram showing a construction of a flat panel X-ray detector included in the X-ray image pickup apparatus according to the embodiment.
Figure 3:
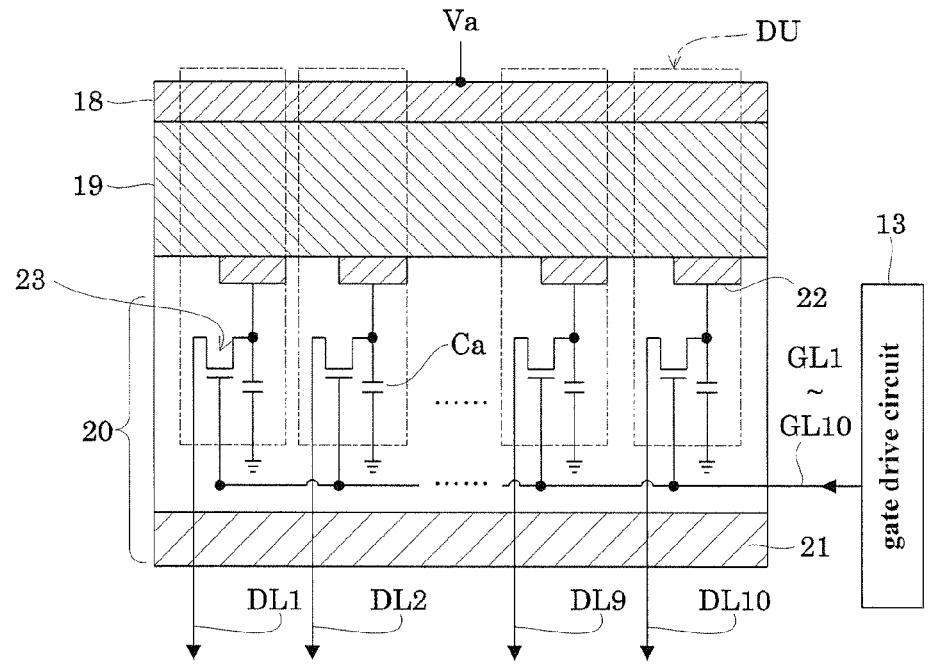
FIG. 3 is a schematic view in vertical section of an X-ray conversion layer and adjacent components of the flat panel X-ray detector included in the X-ray image pickup apparatus according to the embodiment.
Figure 4:
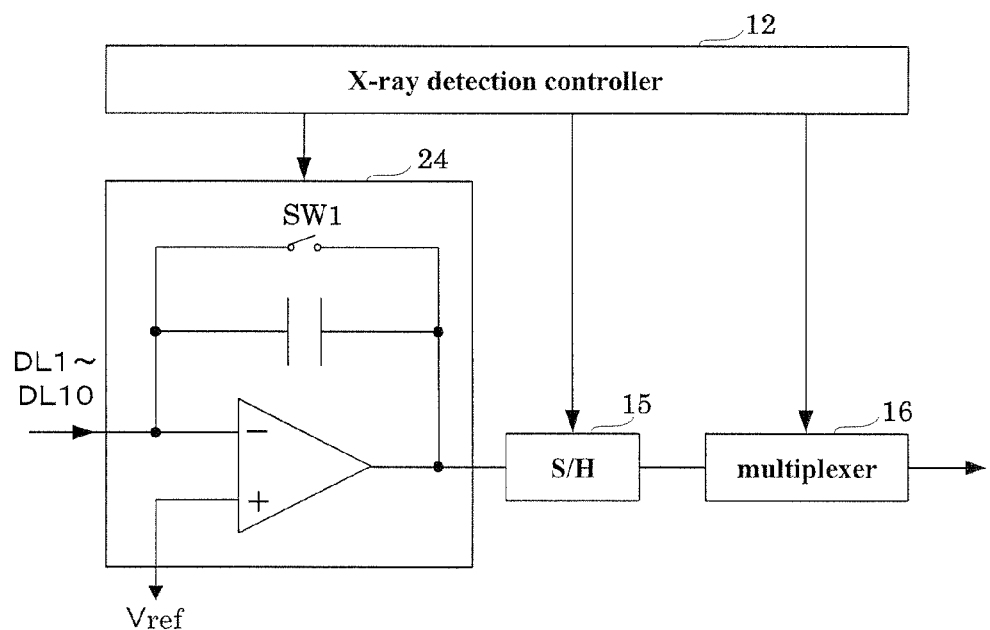
FIG. 4 is a circuit diagram showing a construction of a charge-to-voltage converter according to the embodiment.

FIG. 1 is a block diagram showing an overall construction of an X-ray image pickup apparatus according to the embodiment. FIG. 2 is a block diagram showing a construction of a flat panel X-ray detector included in the X-ray image pickup apparatus. FIG. 3 is a schematic view in vertical section of an X-ray conversion layer and adjacent components of the flat panel X-ray detector. FIG. 4 is a circuit diagram showing a construction of a charge-to-voltage converter. In this embodiment, description will be made taking X-rays as an example of incident light or radiation, and description will be made taking an X-ray image pickup apparatus as an example of radiation image pickup) apparatus.

<X-Ray Image Pickup Apparatus>

As shown in FIG. 1, the X-ray image pickup apparatus includes an X-ray tube 1 for emitting X-rays to a patient M to be imaged, a top board 2 for supporting the patient M, a flat panel X-ray detector (hereinafter called FPD) 3 for converting into charge signals corresponding to the dosage of X-rays transmitted through the patient M (i.e. detecting X-rays as charge signals) and further converting the charge signals into voltage signals for output, an A/D converter 4 for converting, from analog to digital, the voltage signals outputted from the FPD 3, an image processor 5 for processing the digital voltage signals converted by the A/D converter 4 to construct an image, a main controller 6 for carrying out various controls relating to X-ray imaging, an X-ray tube controller 7 for controlling the X-ray tube 1 by generating a tube voltage and a tube current based on the controls by the main controller 6, an input unit 8 capable of inputting settings relating to X-ray image pickup, a display unit 9 for displaying X-ray images processed and produced by the image processor 5 and other information, a storage unit 10 for storing the X-ray images processed and produced by the image processor 5 and other information, and a temperature sensor 11 for measuring temperatures inside the FPD 3. Each component of the X-ray image pickup apparatus will be further described in detail.

As shown in FIG. 2, the FPD 3 has a plurality of X-ray detecting elements DU, an X-ray detection controller 12, a gate drive circuit 13, a charge-to-voltage converter 14, a sample hold unit 15 and a multiplexer 16. The plurality of X-ray detecting elements DU are connected to the gate drive circuit 13 by gate lines GL1-GL10, and are connected to the charge-to-voltage converter 14 by data lines DL1-DL10. The X-ray detection controller 12 is connected to the gate drive circuit 13, charge-to-voltage converter 14, sample hold unit 15 and multiplexer 16. The X-ray detecting elements DU correspond to the detecting elements in this invention. The charge-to-voltage converter 14 corresponds to the charge-to-voltage converting device in this invention.

The temperature sensor 11 is installed inside the FPD 3 for measuring temperature of an X-ray conversion layer 19 and temperature inside the FPD 3, and sending the measured temperatures to the image processor 5 and main controller 6. As the temperature sensor 11, a resistance temperature detector, thermo couple, thermistor or the like may be employed.

The X-ray detecting elements DU output charge signals in response to incident X-rays, and are arranged vertically and horizontally in a two-dimensional matrix form on an X-ray detecting portion XD on which X-rays are incident. FIG. 2 shows, as an example, X-ray detecting elements DU arranged in the two-dimensional matrix form of ten columns×ten rows. On the actual X-ray detecting portion XD, the X-ray detecting elements DU are arranged in the two-dimensional matrix form in the order of 4096 columns×4096 rows, for example.

As shown in FIG. 3, the X-ray detecting elements DU have a voltage application electrode 18 for applying a bias voltage Va of high voltage, an X-ray conversion layer 19 for converting incident X-rays into charge signals, and an active matrix substrate 20 for reading (outputting) the charge signals converted by the X-ray conversion layer 19. The active matrix substrate 20 corresponds to the reading device in this invention.

The X-ray conversion layer 19 consists of an X-ray sensitive semiconductor, and is formed of CdTe or CdZnTe polycrystalline compound semiconductor film. Polycrystalline compound semiconductor film can form the X-ray conversion layer 19 with easy crystal growth and a large area. By using CdTe or CdZnTe as a main raw material for the polycrystalline compound semiconductor film, the X-ray conversion layer 19 can be formed to have excellent response to X-rays and excellent conversion efficiency. It is constructed such that, when X-rays impinge on the X-ray conversion layer 19, a given number of charge signals (carriers) proportional to the energy of X-rays are generated directly (direct conversion type). The generated charge signals are collected separately by pixel electrodes 22, with an electric field generated in the X-ray conversion layer 19 by the bias voltage Va applied to the voltage application electrode 18, As shown in FIG. 3, the active matrix substrate 20 has an insulating glass substrate 21, and on this glass substrate 21 are capacitors Ca for accumulating the charge signals separately collected by the pixel electrodes 22, thin-film transistors (hereinafter called TFTs) 23 acting as switching elements, gate lines GL1-GL10 for controlling the TFTs 23 from the gate drive circuit 13, and data lines DL1-DL10 for reading the charge signals from the TFTs 23.

Next, the X-ray detection controller 12 is controlled from the main controller 6 (see FIG. 1), as shown in FIG. 2, to carry out overall control of the gate drive circuit 13, charge-to-voltage converter 14, sample hold unit 15 and multiplexer 16, and carry out controls to take out successively and selectively the charge signals detected by the X-ray detecting elements DU to the charge-to-voltage converter 14, and further to output them successively from the multiplexer 16. Specifically, the X-ray detection controller 12 is constructed to output a gate actuating signal for starting operation of the gate drive circuit 12, an amplifier resetting signal for starting amplifier resetting of the charge-to-voltage converter 14, a sample hold control signal for controlling sample holding of the sample hold unit 15, and a multiplexer control signal for controlling operation of the multiplexer 16.

Next, the gate drive circuit 13 operates the TFT 23 of each X-ray detecting element DU to take out successively and selectively the charge signals detected by the X-ray detecting elements DU. The gate drive circuit 13, based on the gate actuating signal from the X-ray detection controller 12, successively selects the gate lines GL1-GL10 commonly connected to the respective rows of X-ray detecting elements DU, and transmits a gate signal thereto. The TFTs 23 of X-ray detecting elements DU in a selected row are turned on all at once by the gate signal, to output the charge signals accumulated in the capacitors Ca to the charge-to-voltage converter 14 through the data lines DL1-DL10.

Next, the charge-to-voltage converter 14 includes charge-to-voltage converting amplifiers 24 as shown in FIG. 4, which correspond in number (ten in FIG. 2) to the data lines DL1-DL10 provided for the respective columns of X-ray detecting elements DU. The charge-to-voltage converting amplifiers 24 are charge sensitive amplifiers (CSA) for converting the charge signals outputted from the respective X-ray detecting elements DU into voltage signals. The charge-to-voltage converting amplifiers 24 convert the charge signals read from the data lines DL1-DL10 into the voltage signals for output to the sample hold unit 15. The charge-to-voltage converter 14 corresponds to the charge-to-voltage converting device in this invention.

Next, the sample hold unit 15 includes sample hold circuits corresponding in number to the number of charge-to-voltage converting amplifiers 24. Based on the sample hold control signal from the X-ray detection controller 12, the voltage signals outputted from the charge-to-voltage converting amplifiers 24 are sampled at a predetermined time, the voltage signals are held upon elapse of the predetermined time, and voltage signals in a stable state are outputted to the multiplexer 16.

Next, the multiplexer 16 has, mounted inside, switches corresponding in number to the number of sample hold circuits. Based on the multiplexer control signal from the X-ray detection controller 12, the switches are switched to ON state one after another, to output to the A/D converter 4 a time sharing signal which bundles each of the voltage signals outputted from the sample hold circuits. The A/D converter 4 samples the voltage signals from the multiplexer 16 with predetermined timing, converts them into digital voltage signals, and outputs them to the image processor 5.

<Image Processor>

As shown in FIG. 1, the image processor 5 has, in its interior, an image memory unit 25, an offset signal removing unit 26, a dark current noise calculating unit 27, a noise variation calculating unit 28, a noise variation removing unit 29 and an image constructing unit 30. The image processor 5 constructs an X-ray fluoroscopic image by removing offset signals and temperature variation noise from the voltage signals transferred from the FPD 3 through the A/D converter 4.

First, what type of signals the voltage signals transferred to the image processor 5 are will be described. The voltage signals transferred to the image processor 5 (hereinafter called the detection voltage signals) can be divided into three components according to the cause of generation. That is, the detection voltage signals are formed of X-ray fluoroscopic image signals for reconstructing an X-ray fluoroscopic image, dark current noise Nt caused by dark current flowing through the X-ray conversion layer, and amplifier noise Mt generated when the voltage signals are amplified by the charge-to-voltage converter 14, for example.

$$(\text{detection voltage signals}) = (\text{X-ray fluoroscopic image signals}) + Nt + Mt \tag{1}$$

The X-ray fluoroscopic image signals are voltage signals based on the charge signals converted by the X-ray conversion layer 19 from X-rays transmitted through the patient M, and are voltage signals required to reconstruct an X-ray transmission image.

The dark current noise Nt is a noise signal converted as a voltage signal from dark current flowing within the X-ray conversion layer 19, and its value is sensitively varied with temperature T of the X-ray conversion layer 19. Generally, the dark current noise Nt can be expressed by the following equation.

$$Nt=\alpha(\exp(\beta/T)-1)(\alpha,\beta\text{:constants},T\text{:absolute temperature[K]}) \quad (2)$$

The amplifier noise Mt is a noise signal produced by amplification action of the amplifiers in the charge-to-voltage converter 14. Although the amplifier noise Mt will also vary with temperature variation, its variation is markedly small compared with the variation of the dark current noise Nt in response to temperature. The amplifier noise Mt is removable only by acquiring offset signals periodically.

Figure 5:
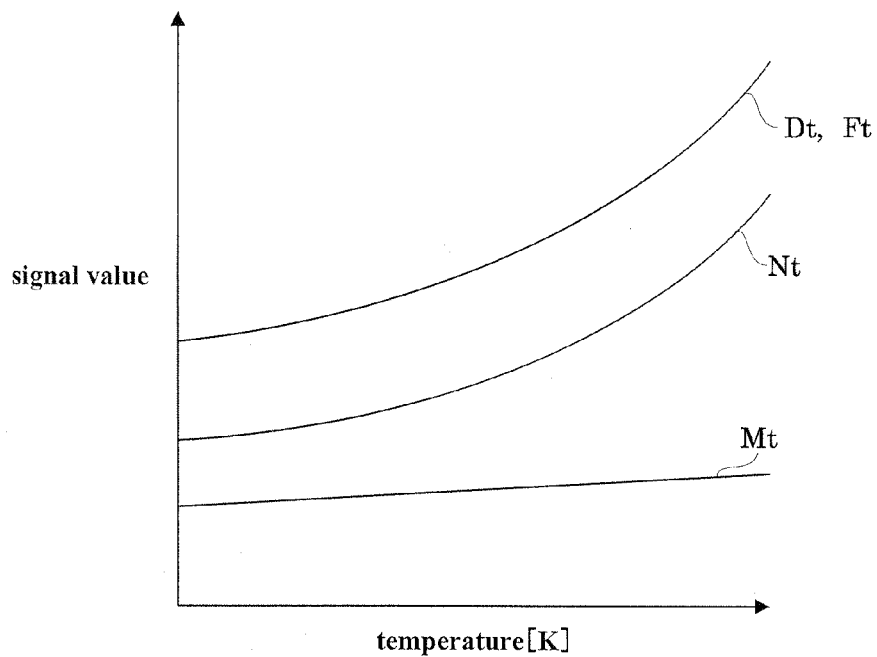
FIG. 5 is a graph showing a relationship between noise signals included in detection voltage signals and temperature according to the embodiment.

Both the dark current noise Nt and amplifier noise Mt reduce the dynamic range of the X-ray fluoroscopic image signals. Further, the temperature of the environment in which the X-ray imaging apparatus is installed, in spite of air-conditioning, always changes from moment to moment. An accurate fluoroscopic image cannot be obtained when the dark current noise Nt appears on the fluoroscopic image due to temperature change. FIG. 5 shows dark current noise Nt and amplifier noise Mt. The dark current noise Nt changes exponentially with temperature T because of the nature of dark current. The amplifier noise Mt changes gently with temperature T.

A total noise signal Dt (see FIG. 5) which is a sum of these dark current noise Nt and amplifier noise Mt can be determined accurately by acquiring offset signals Ft which are detection voltage signals acquired when X-rays are not emitted from the X-ray tube 1.

$$Dt = Nt + Mt \quad (3)$$
$$= Ft \quad (4)$$

Figure 6:
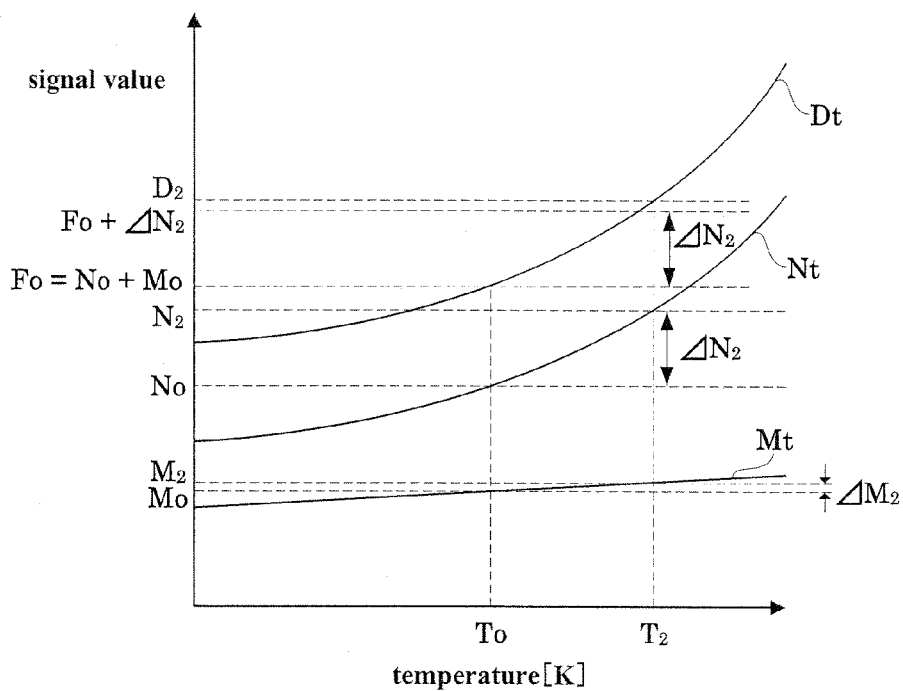
FIG. 6 is a graph showing a relationship between noise signals included in detection voltage signals and temperature according to the embodiment.

Here, when, as shown in FIG. 6, the time interval between the time of acquiring offset signals Fo at a certain temperature To and the time of X-ray image pickup at a temperature $T_2$ is short, the difference in temperature of the FPD 3 between the two points of time is small. Therefore, the difference $\Delta M_2$ (=$M_2$−Mo) between amplifier noise $M_2$ at the time of X-ray image pickup and amplifier noise Mo at the time of acquiring the offset signals Fo is minute, which enables an assumption Mo≈$M_2$. As a result, total noise signals Dt at the time of X-ray image pickup can be expressed as follows using temperature variation noise $\Delta N_2$.

$$\begin{aligned} D_2 &= N_2 + M_2 & (5)\\ &\approx N_2 + Mo & (\because Mo \approx M_2)\\ &= (\Delta N_2 + No) + Mo & (\because \Delta N_2 = N_2 - No)\\ &= \Delta N_2 + Fo & (\because Fo = No + Mo) \end{aligned}$$

Here, the temperature variation noise $\Delta N_2$ is a difference between dark current noise $N_2$ included in the detection voltage signals at the time of X-ray image pickup and dark current noise No included in the offset signals Fo at the time of acquiring the offset signals Fo. Since $\Delta N_2=0$ when the temperature condition is the same at the time of X-ray image pickup and at the time of acquiring the offset signals Fo, the detection voltage signals are formed of two components.

$$\text{(detection voltage signal)}=\text{(X-ray fluoroscopic image signal)}+Fo,\text{(provided that temperature is constant)} \quad (6)$$

Consequently, if the temperature characteristic of dark current noise Nt is determined beforehand, even if the temperature of the X-ray conversion layer 19 changes after the offset signals Fo are acquired, dark current noise Nt and amplifier noise Mt can be removed from the detection voltage signals by measuring the temperature of the X-ray conversion layer 19. So, a method of measuring dark current noise Nt with high accuracy will be described hereinafter.

Figure 7:
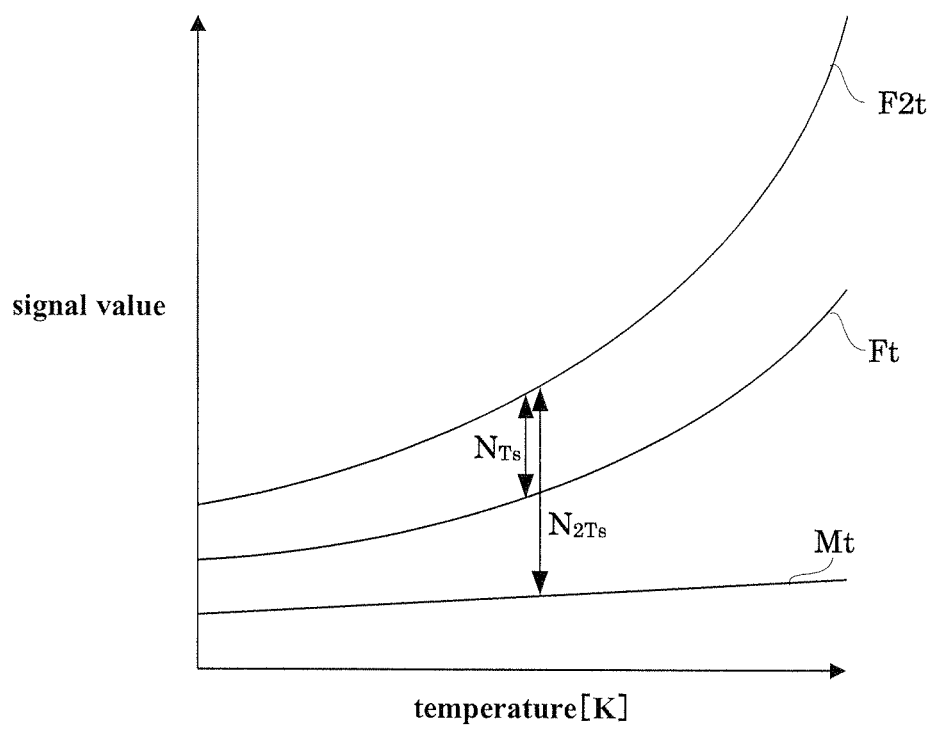
FIG. 7 is a graph showing a relationship between noise signals included in detection voltage signals and temperature according to the embodiment.

The values of $\alpha$ and $\beta$ in equation (2) are values variable with the component material and construction state of the X-ray conversion layer 19. So, as shown in FIG. 7, offset signals are acquired by changing the time for accumulating charge signals in the capacitors Ca, and a difference therebetween is determined, thereby to determine dark current noise Nt at that temperature. That is, under the same temperature condition, offset signals $F_{Ts}$ obtained by accumulating charge signals for a time Ts are subtracted from offset signals $F_{2Ts}$ obtained by accumulating charge signals in the capacitors Ca for a time 2Ts, thereby to be able to measure dark current noise Nt at that temperature. Here, time Ts is assumed to be an actual time for accumulating charge signals in the capacitors Ca when carrying out an X-ray image pickup. Thus, the temperature characteristic of dark current noise Nt can be determined by measuring, for each temperature, a difference between offset signals acquired by changing the time for accumulating charge signals in the capacitors Ca. This temperature characteristic of dark current noise Nt may be obtained as an approximate expression as in equation (2), or may be obtained as a look-up table corresponding to each temperature.

Figure 8:
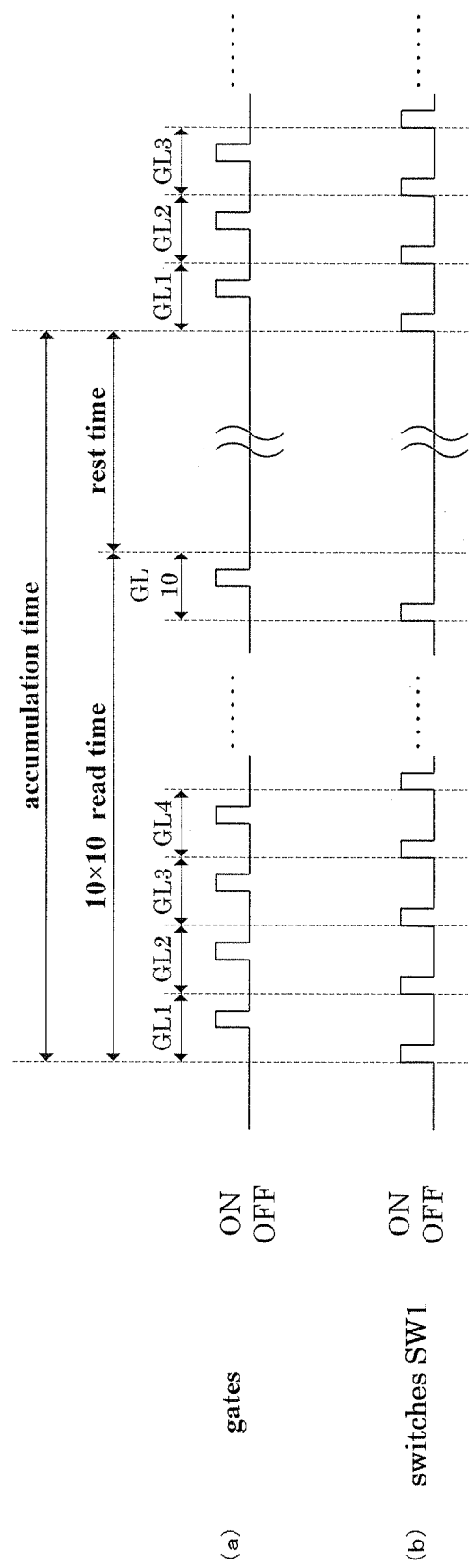
FIG. 8 is a timing chart of reading charge signals with changes made in the time of storage in capacitors according to the embodiment.

For changing the time for accumulating charge signals in the capacitors Ca, as shown in FIG. 8, an adjustment can be made by controlling ON/OFF time of the gates and ON/OFF time of the switches SW1 of the charge-to-voltage converting amplifiers 24. This control is carried out by the X-ray controller 12 controlling the gate drive circuit 13 and charge-to-voltage converter 14, respectively.

First, the case of accumulating charge signals in the capacitors Ca for the time Ts will be described. At a time of acquiring dark image signals, as shown in FIG. 8(a), when GL1-GL10 are successively selected to put in ON state the gates in the detecting elements DU connected to each gate line, the charge signals accumulated in the capacitors Ca are read to the charge-to-voltage converter 14 in order. In the charge-to-voltage converter 14, the read charge signals are inputted to the charge-to-voltage converting amplifiers 24 connected to the respective data lines. In the charge-to-voltage converting amplifiers 24, as shown in FIG. 8(b), the switches SW1 are once put in ON state to initialize the charge-to-voltage converting amplifier 24 immediately before the gates are put in ON state, and thereafter the inputted charge signals are amplified while being converted into voltage signals. When GL1 to GL10 have been selected successively to complete readout of two-dimensional image information, there occurs a rest time for keeping the gates and switches SW1 in OFF state for a certain period of time. At a time of dynamic image pickup, an X-ray image pickup for a next frame is carried out during this rest period. That is, the accumulation time Ts is a time combining the read time for reading the charge signals from the 10×10 X-ray detecting elements DU and the rest time. The accumulation time Ts, preferably, is a time for accumulating charge signals in the capacitors Ca at a time of actual X-ray image pickup. In this way, offset signals FTs are obtained from the charge signals accumulated in the capacitors Ca for the time Ts. Signal components of the offset signals $F_{Ts}$ are as follows.

$$F_{Ts} = N_{Ts} + M_{Ts} \tag{7}$$

Next, the case of accumulating charge signals for the time 2Ts which is twice the time Ts noted above for accumulating charge signals in the capacitors Ca will be described. At a time of acquiring dark image signals, charge signals are accumulated in the capacitors Ca for the time 2Ts which is twice the time Ts by adjusting the rest time shown in FIG. 8. Then, the gates are put in ON state successively to read the charge signals accumulated in the capacitors Ca to the charge-to-voltage converter 14. In this way, offset signals $F_{2Ts}$ can be obtained from the charge signals accumulated in the capacitors Ca for the time 2Ts. Since the operating time of the amplifiers of the charge-to-voltage converting amplifiers 24 is the same as at the time of acquiring the offset signals $F_{Ts}$, amplifier noise signals generated in the acquired offset signals have the same value. Since the dark current noise Nt is proportional to the time that the charge signals generated by the dark current flowing through the X-ray conversion layer 19 are accumulated in the capacitors Ca, the signal components of the offset signals $F_{2Ts}$ are as follows.

$$F_{2Ts} = N_{2Ts} + M_{Ts} \tag{8}$$
$$= 2 \times N_{Ts} + M_{Ts}$$

Based on equation (7) and equation (8), dark current variation noise $N_{Ts}$ can be determined accurately by subtracting the offset signals $F_{Ts}$ acquired for the time Ts which is a half of the time for accumulating the charge signals in the capacitors Ca, from the offset signals $F_{2Ts}$ acquired by accumulating the charge signals in the capacitors Ca for the time 2Ts.

$$F_{2Ts} - F_{Ts} = (2 \times N_{Ts} + M_{Ts}) - (N_{Ts} + M_{Ts}) \tag{9}$$
$$= N_{Ts}$$

As described above, from the offset signals obtained by changing the time for accumulating the charge signals in the capacitors Ca, the dark current noise Nt at that temperature can be determined with high accuracy. The temperature characteristic of dark current noise Nt can be determined with high accuracy by obtaining the dark current noise Nt while changing the temperature of the X-ray conversion layer 19. For example, an approximate expression of dark current noise Nt can be obtained by determining the two constants α and β. The more temperatures and offset signals measured will enable the more accurate approximate expression to be obtained. A look-up table of the relationship between temperature and dark current noise Nt may be created instead of the approximate expression. Thus, an approximate expression or look-up table of temperature and dark current noise Nt for each detecting element DU can be created.

Next, each component of the image processor 5 which obtains X-ray fluoroscopic image signals from the detection voltage signals will be described.

The digital voltage signals outputted from the A/D converter 4 are temporarily stored in the image memory unit 25.

The offset signal removing unit 26 stores offset signals acquired when dark images are picked up periodically. The stored offset signals are updated whenever a dark image is picked up. The offset signal removing unit 26 removes the offset signals from the detection voltage signals sent from the image memory unit 25, and sends removed values to the noise variation removing unit 29.

The dark current noise calculating unit 27 has a temperature conversion approximate expression or a look-up table which is the temperature characteristic of dark current noise Nt, and calculates dark current noise Nt based on temperature information sent from the temperature sensor 11. A construction using either the temperature conversion approximate expression or the look-up table may be adopted, or a separate use may be adopted such that the temperature conversion approximate expression is used to correct temperature with high precision at the time of still image pickup, and the look-up table is used to correct temperature at high speed at the time of dynamic image. Dark current noise No at temperature To at the time of picking up dark images periodically, and dark current noise $N_2$ at temperature $T_2$ at the time of X-ray image pickup, respectively, are calculated and sent to the noise variation calculating unit 28.

Figure 9:
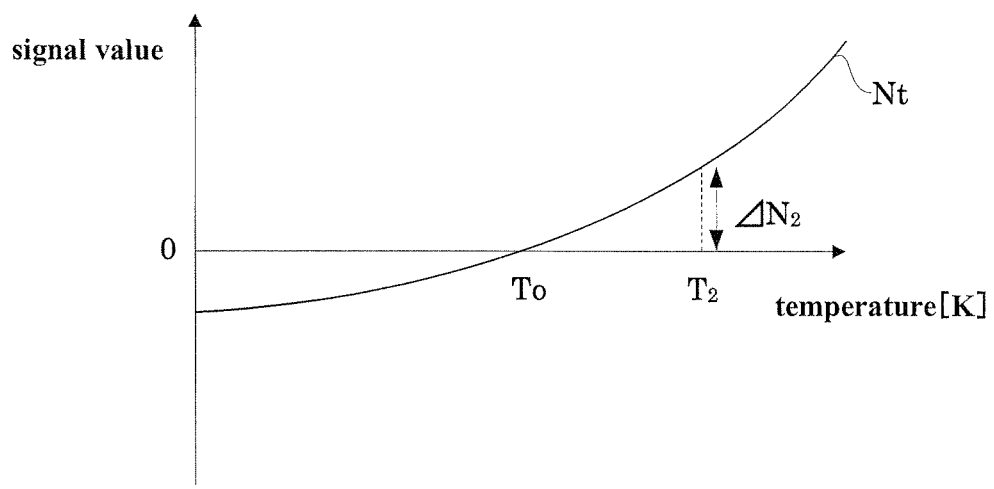
FIG. 9 is a graph showing a relationship between dark current noise signals and temperature according to the embodiment.
Figure 10:
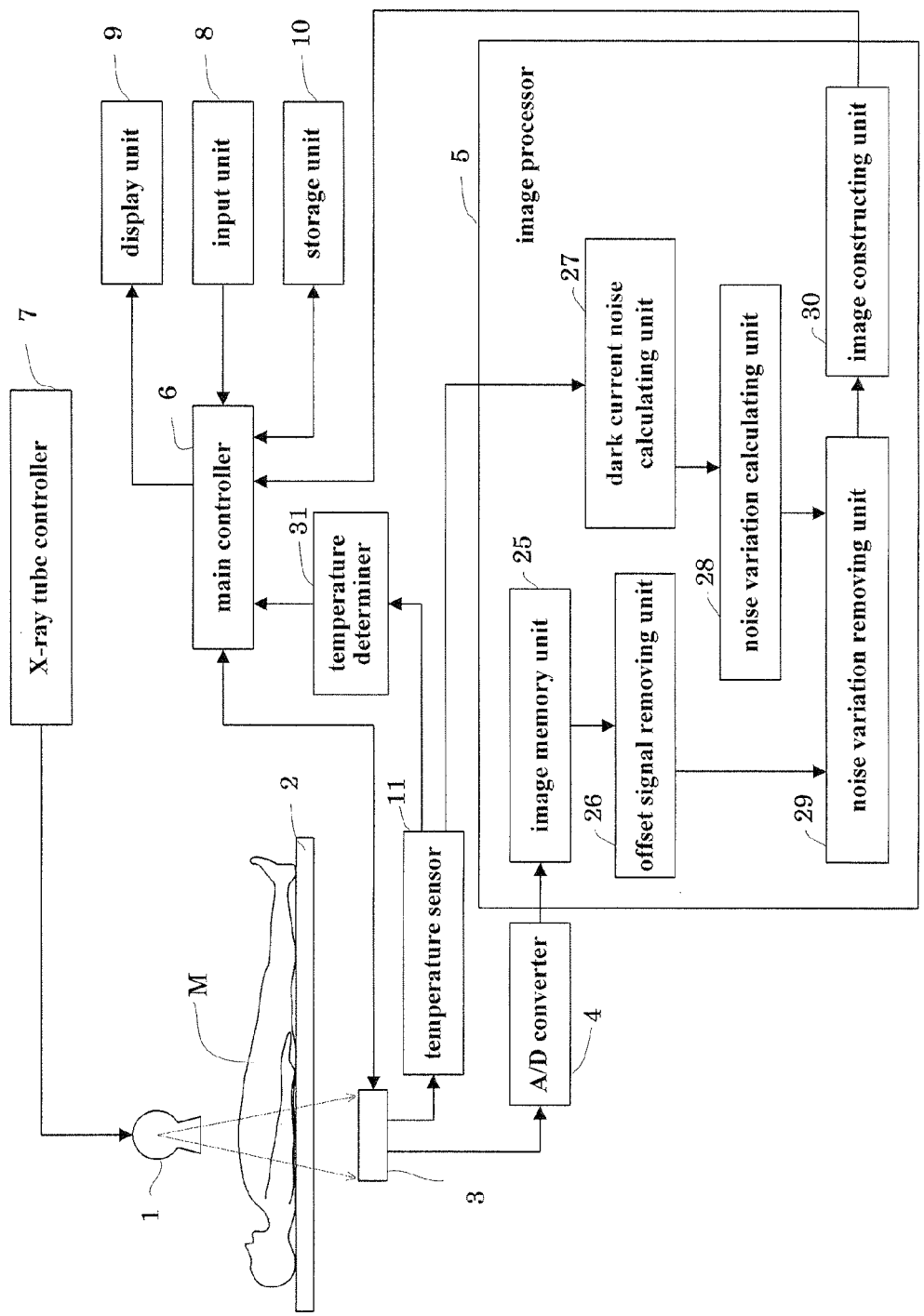
FIG. 10 is a block diagram showing a construction of an X-ray image pickup apparatus according to another embodiment of this invention.

The noise variation calculator 28, as shown in FIG. 9, regards dark current noise component No at temperature To at the time of picking up dark images periodically as zero point, and calculates temperature variation noise $\Delta N_2$ which is a difference to the dark current noise Nt at temperature $T_2$ at the time of X-ray image pickup. The calculated temperature variation noise $\Delta N_2$ is sent to the noise variation removing unit 29.

The noise variation removing unit 29 removes temperature variation noise $\Delta N_2$ calculated from the detection voltage signals with the offset signals Fo removed therefrom, thereby to acquire an X-ray fluoroscopic image signal for each X-ray detecting element DU.

The image constructing unit 30 constructs an X-ray transmission image from the X-ray fluoroscopic image signals. Not only the transmission image but a tomogram can also be reconstructed at a time of CT image pickup. The constructed X-ray transmission image is transferred to the main controller 6 to be displayed on the display unit 9 or stored in the storage unit 10.

<X-Ray Image Pickup>

Next, operation of the X-ray imaging apparatus in this embodiment for performing X-ray image pickup will be described using FIGS. 1 through 4.

First, the operator can set a cycle of acquiring the offset signals from the input unit 8, and sets, for example, intervals of ten minutes for acquiring the offset signals. In response to this setting the main controller 6 instructs the X-ray tube controller 7 and the X-ray detection controller 12 of FPD 3 to acquire the offset signals every ten minutes. Next, when an X-ray image pickup start is instructed at the input unit 8, the main controller 6 will control the X-ray tube controller 7 and X-ray detection controller 12. Based on the control from the main controller 6, the X-ray tube controller 7 generates the tube voltage and tube current to control the X-ray tube 1, whereby X-rays are emitted from the X-ray tube 1 to the patient M. X-rays transmitted through the patient M are converted by the X-ray detecting elements DU of FPD 3 into charge signals corresponding to the dosage of X-rays transmitted through the patient M, which are accumulated in the capacitors Ca.

Next, the X-ray detection controller 12 outputs the gate actuating signal to the gate drive circuit 13. In response to this gate actuating signal, the gate drive circuit 13 selects the gate lines successively. In this embodiment, description is made on an assumption that the gate lines G1, G2, G3, . . . , G9 and G10 are selected one after another in the stated order. The gate drive circuit 13 selects the gate line G1, whereby the respective detecting elements DU connected to the gate line G1 are designated. Voltage is applied by the transmitted gate signal to the gates of the TFTs 23 of the respective detecting elements DU designated, to become ON state. Consequently, the carriers accumulated in the capacitors Ca connected to the respective TFTs 23 designated are read to the data lines DL1-DL10 via the TFTs 23. Next, the gate drive circuit 13 selects the gate line G2, and through the same procedure, the respective detecting elements DU connected to the gate line G2 are designated, and the charge signals accumulated in the capacitors Ca connected to the respective detecting elements DU designated are read to the data lines DL1-DL10. By similarly selecting the remaining gate lines G3-G10 in order, the charge signals are read in two dimensions.

In this way, the gate drive circuit 13 selects the gate lines GL1-GL10 successively, whereby the detecting elements DU connected to each gate line are designated. The charge signals accumulated in the capacitors Ca of the respective detecting elements DU designated are read to the data lines DL1-DL10.

The charge signals read to the data lines are amplified while being converted into voltage signals in the charge-to-voltage converting amplifiers 24 in the charge-to-voltage converter 14. And the sample hold unit 15 samples and once holds the voltage signals converted by the charge-to-voltage converter 14. Subsequently the multiplexer 16 outputs successively as time sharing signals the voltage signals held by the sample hold unit 15. The outputted voltage signals are converted from analog values into digital values by the A/D converter 4. The voltage signals converted into digital values are sent to the image processor 5.

The voltage signals (detection voltage signals) sent to the image processor 5 are stored in the image memory unit 25. Next, the detection voltage signals are sent from the image memory unit 25 to the offset signal removing unit 26. The offset signal removing unit 26 has stored therein the offset signals acquired periodically, for example, at intervals of ten minutes, and removes these offset signals from the detection voltage signals. However, since the temperatures of the FPD 3 and X-ray detection layer 19 are different between the time of acquiring the offset signals and the time of X-ray image pickup, the detection voltage signals with the offset signals removed therefrom have the noise due to this temperature change still remaining therein.

Next, the dark current noise calculating unit 27, having received the temperature To at the time of acquiring the offset signals from the temperature sensor 11 when the offset signals are acquired, calculates dark current noise No at the time of acquiring the offset signals from the temperature characteristic of dark current noise Nt, and transfers the dark current noise No to the noise variation calculating unit 28. Also at the time of X-ray image pickup, the temperature $T_2$ when the X-ray image is picked up has been sent from the temperature sensor 11 to the dark current noise calculating unit 27, which calculates dark current noise $N_2$ from the temperature characteristic of dark current noise Nt, and sends the dark current noise $N_2$ to the noise variation calculator 28.

The noise variation calculator 28 calculates temperature variation noise $\Delta N_2$ by subtracting the dark current noise No at the time of acquiring the offset signals from the dark current noise $N_2$ at the time of X-ray image pickup. This calculated temperature variation noise $\Delta N_2$ is sent to the noise variation removing unit 29.

The noise variation removing unit 29 further removes the temperature variation noise $\Delta N_2$ from the detection voltage signals having the offset signals Fo removed therefrom. The dark current noise sensitively varying with the temperature change of the FPD 3 and X-ray conversion layer 19 can be removed with temperature variations. The detection voltage signals with the offset signals Fo and temperature variation noise $\Delta N_2$ removed therefrom are sent to the image constructing unit 30 which constructs an X-ray fluoroscopic image or CT image. The constructed X-ray, fluoroscopic image or CT image is displayed on the display unit 9 or stored in the storage unit 10 through the main controller 6.

According to this embodiment, as described above, even if the temperature of the X-ray conversion layer 19 changes between the time of acquiring the offset signals periodically, for example, at intervals of ten minutes, and the time of executing an X-ray image pickup, the dark current noise can be removed with high accuracy according to the temperature change. That is, noise signals can be removed with high accuracy by calculating temperature variation noise $\Delta Nt$ which is a variation from the time of acquiring the offset signals of dark current noise Nt sensitive to temperature change, from the temperature characteristic of dark current noise Nt. This is realized by deriving with high accuracy the dark current noise Nt caused by dark current flowing in the X-ray conversion layer, from the offset signals accumulated in the capacitors Ca at different times, and measuring dark current noise Nt at different temperatures, thereby determining the temperature characteristic of dark current noise Nt beforehand.

Since what is necessary is just to calculate and remove only the temperature variation noise $\Delta Nt$ which is a variation for the dark current noise No at the time of acquiring dark image signals Fo, it is not necessary to acquire the dark image signals Fo frequently, and the temperature correction of dark current noise Nt can be made with high accuracy even when emitting light or radiation continuously. Thus, since the offset signals Fo may be acquired periodically, the temperature correction of the noise signals included in the detection voltage signals can be carried out properly to realize high definition imaging also when images are picked up continuously such as at a time of dynamic image pickup, for example.

This invention is not limited to the foregoing embodiment, but may be modified as follows.

(1) In the foregoing embodiment, the offset signals Fo are acquired periodically. A construction may be adopted in which comparison is made between a threshold value set for temperatures To at the time of acquiring the offset signals and temperatures measured at intervals of time from the temperature sensor 11, and an offset signal Fo is acquired again when a temperature determiner 31 determines that a temperature measured is higher or lower than the threshold value. That is, the temperature determiner 31 sends a command to the main controller 6 to acquire an offset signal again when the temperature T has changed to such an extent that the amplifier noise Mo included in the offset signal Fo and the amplifier noise Mt at temperature T measured by the temperature sensor 11 cannot be approximated to the same value. Consequently, the main controller 6 sends instructions to the X-ray tube controller 7 to stop emission from the X-ray tube 1, and to the X-ray detection control unit 12 to acquire an offset signal. Thus, instead of acquiring the offset signals Fo periodically, the temperature change of the X-ray detection layer 19 is monitored constantly, and an offset signal Fo is acquired again when a variation between the temperature at the time of acquiring the offset signal Fo and the current temperature exceeds a tolerance level. This can attain a differentiation of image quality by selecting an appropriate tolerance level of temperature change.

(2) In the foregoing embodiment, the temperature variation noise $\Delta N_2$ is removed after the offset signals Fo are removed from the detection voltage signals. This is not limitative. The offset signals Fo may be removed after the temperature variation noise $\Delta N_2$ is first removed from the detection voltage signals. The offset signals Fo and temperature variation noise $\Delta N_2$ may be removed from the detection voltage signals at the same time.

(3) In the foregoing embodiment, the temperature characteristic of dark current noise for each X-ray detecting element DU is used by the dark current noise calculating unit 27. A temperature characteristic of dark current noise may be obtained beforehand for each area having X-ray detecting elements DU, and temperature variation noise of each X-ray detecting element DU may be calculated using this temperature characteristic of each area. This can further speed up the temperature correction of the detection voltage signals.

(4) In the foregoing embodiment, the X-ray detecting elements DU are X-ray sensitive semiconductors in response to X-rays. Employing light sensitive semiconductors will enable manufacture of a light image pickup apparatus which can remove the temperature variation noise of the conversion layer with the same construction and with high accuracy.

The invention claimed is:

1. A light or radiation image pickup apparatus comprising:
   a conversion layer for converting light or radiation into charge signals;
   detecting elements corresponding to respective capacitors for accumulating the charge signals, the conversion layer being divided into a two-dimensional matrix form corresponding to the detecting elements;
   a reading device for reading the charge signals accumulated in the capacitors;
   a charge-to-voltage converting device for converting the charge signals read from the reading device into voltage signals;
   a temperature measuring device for measuring temperatures of the conversion layer;
   a dark current noise calculating unit for calculating dark current noises generating from dark current flowing through the conversion layer, from a dark current noise temperature characteristic obtained beforehand at times of dark images by varying time for accumulating the charge signals in the capacitors, and the temperatures measured by the temperature measuring device;
   a dark image signal removing unit for removing dark image signals from the voltage signals;
   a noise variation calculating unit for calculating a variation between a dark current noise at a temperature at a time of dark image signal acquisition and a dark current noise at a temperature at a time of image pickup, calculated by the dark current noise calculating unit; and
   a noise variation removing unit for removing the dark current noise variation calculated by the noise variation calculating unit from the voltage signals.

2. The light or radiation image pickup apparatus according to claim 1, wherein the dark image signals are acquired periodically.

3. The light or radiation image pickup apparatus according to claim 1, comprising:
   a temperature determiner for determining whether the temperatures measured by the temperature measuring device exceed a predetermined temperature range;
   wherein the dark image signals are acquired when the temperature determiner determines that the temperatures measured by the temperature measuring device exceed the predetermined temperature range.

4. The light or radiation image pickup apparatus according to claim 1, wherein the dark current noise calculating unit stores the dark current noise temperature characteristic as an approximate expression.

5. The light or radiation image pickup apparatus according to claim 1, wherein the dark current noise calculating unit stores the dark current noise temperature characteristic as a look-up table.

6. The light or radiation image pickup apparatus according to claim 1, wherein the light or radiation conversion layer is a polycrystalline compound semiconductor.

7. The light or radiation image pickup apparatus according to claim 6, wherein the light or radiation conversion layer has CdTe or CdZnTe as a main raw material.

* * * * *